(12) United States Patent
Yukawa

(10) Patent No.: US 7,598,063 B2
(45) Date of Patent: Oct. 6, 2009

(54) PROCESS FOR PRODUCING ETHANOL BY USING RECOMBINANT CORYNEFORM BACTERIUM

(75) Inventor: Hideaki Yukawa, Kyoto (JP)

(73) Assignee: Research Institute of Innovative Technology for the Earth, Kyoto (JP)

( * ) Notice: Subject to any disclaimer, the term of this patent is extended or adjusted under 35 U.S.C. 154(b) by 0 days.

(21) Appl. No.: 10/296,947

(22) PCT Filed: Jun. 12, 2001

(86) PCT No.: PCT/JP01/04935

§ 371 (c)(1),
(2), (4) Date: Dec. 12, 2002

(87) PCT Pub. No.: WO01/96573

PCT Pub. Date: Dec. 20, 2001

(65) Prior Publication Data

US 2004/0072312 A1    Apr. 15, 2004

(30) Foreign Application Priority Data

Jun. 16, 2000 (JP) .................... 2000-181625

(51) Int. Cl.
| | |
|---|---|
| *C12P 7/06* | (2006.01) |
| *C12N 9/02* | (2006.01) |
| *C12N 9/04* | (2006.01) |
| *C12N 1/20* | (2006.01) |
| *C12N 15/00* | (2006.01) |
| *C12Q 1/68* | (2006.01) |
| *C07H 21/04* | (2006.01) |
| *C12Q 1/00* | (2006.01) |
| *C12Q 1/26* | (2006.01) |
| *C12Q 1/32* | (2006.01) |
| *C12P 21/04* | (2006.01) |

(52) U.S. Cl. ............... 435/161; 435/4; 435/6; 435/26; 435/25; 435/252.3; 435/320.1; 435/440; 435/189; 435/69.1; 435/71.1; 435/190; 536/23.2; 536/23.4

(58) Field of Classification Search .......... 435/232, 435/190, 161, 252.3, 320.1, 71.1, 252.32, 435/69.1, 4, 6, 26, 440, 189; 536/23.2, 23.7
See application file for complete search history.

(56) References Cited

U.S. PATENT DOCUMENTS 4,690,897 A * 9/1987 Squires et al. ........... 435/320.1
4,965,197 A * 10/1990 Liebl et al. ................ 435/69.8
5,482,846 A    1/1996 Ingram et al.
5,693,781 A   12/1997 Zupancic et al.

FOREIGN PATENT DOCUMENTS

| EP | 0 803 575 A1 * | 10/1997 |
|---|---|---|
| JP | H7-59187 | 6/1999 |
| WO | WO 90/02193 | 3/1990 |
| WO | WO 92/10561 | 6/1992 |
| WO | WO 92/16615 | 10/1992 |
| WO | WO 03/025117 | 3/2003 |

OTHER PUBLICATIONS

Bianchi et al. Mol. Microbiol. Jan. 1996; 19(1):abstract.*
"Corynebacteria" —Web printout—1995.*
ExPASy database: alcohol dehydrogenase.*
ExPASy database: pyruvate dehydrogenase.*
Hua et al. Biochemical Engineering Journal 2 (1998) 89-100.*
Inui et al. Metabolic engineering of Corynebacterium glutamicum for fuel ethanol production under oxygen-deprivation conditions. J Mol Microbiol Biotechnol. 2004;8(4):243-54.*
ExPASy database: alcohol dehydrogenase, (2005).*
ExPASy database: pyruvate decarboxylase, (2005).*
Yukawa et al., " Development of New Bioprocess with Non-lytic Coryneform Bacteria", *Bio Science to Industry*, (1992), vol. 50, No. 3, pp. 213-217.
Terasawa et al., "Living cell reaction process for L-isoleucine and L-valine production", *Journal of Industrial Microbiology*, 5 (1990), pp. 289,294.
Kurunushi et al., "Bio Process ha Hakkou-hou ka Kouso-hou ka soretomo••", *Kagaku Gujutsushi MOL*, (1989), vol. 27, No. 10, pp. 74-79.
Yukawa, "Production of Fuel Ethanol from Biomass", *Kagaku Keizai*, (Nov. 2000), vol. 47, pp. 87-92.
Yukawa, "Production of Fuel Ethanol from Biomass", *Bio Industry*, (Mar. 2001), vol. 18, No. 3, pp. 80-85.
Ingram, et al "Enteric bacterial catalysts for fuel ethanol production," Biotechnol Prog. Sep.-Oct. 1999;15(5):855-66.
Funke G, et al. "Clinical microbiology of coryneform bacteria," Clin Microbiol Rev. Jan. 1997;10(1):125-59. Review.
Velizarov, et al., "Production of L-lysine by free ans PVA-cryogel immobilized corynebacteriumglutamicum cells," Database Biosis 'Online! 1992 XP002345539, *abstract* & Biotechnology Letters, 14, 1992, 291-296.

* cited by examiner

*Primary Examiner*—Yong D Pak
(74) *Attorney, Agent, or Firm*—Jacobson Holman PLLC

(57) ABSTRACT

The present invention provides a process for highly efficiently producing ethanol at a high productivity consisting of using a coryneform bacterium which has been transformed by a DNA containing a gene expressing pyruvate decarboxylase activity and, if desired, a gene expressing alcohol dehydrogenase activity under a regulatory sequence allowing for the expression, under ethanol production conditions wherein this bacterium does not substantially proliferate to produce ethanol.

2 Claims, No Drawings

PROCESS FOR PRODUCING ETHANOL BY USING RECOMBINANT CORYNEFORM BACTERIUM

This is a nationalization of PCT/JP01/04935, filed Jun. 12, 2001 and published in Japanese.

FIELD OF THE INVENTION

The present invention relates to a process for producing ethanol. Particularly, the present invention relates to a process of producing ethanol wherein sugars such as glucose are used as raw material, and more particularly, a process for highly efficiently producing ethanol at a high productivity consisting of using a coryneform bacterium which has been transformed by a DNA containing gene expressing pyruvate decarboxylase (referred to hereinafter as PDC) activity and, if desired, a gene expressing alcohol dehydrogenase(referred to hereinafter as ADH) activity under a regulatory sequence allowing the expression, and fermenting a raw material, sugars such as glucose, under ethanol production conditions wherein this bacterium does not substantially proliferate to produce ethanol, which is then collected.

BACKGROUND ART

Up to now, ethanol has been prepared by chemical synthesis via ethylene from fossil resources such as coal and petroleum, or a fermentation of sugars from biomass resource such as plant by a microorganism such as yeast or bacteria. Among these, a process for producing ethanol by fermentation using a renewable biomass resource in light of energy resource or environmental problems has been noticed.

A process for producing ethanol by a conventional large-scale industrial fermentation is a process by fermenting starch or sugars from various biomass resources, namely, a technology based on a brewage for potable ethanol. However, the use of a yeast as a fermentation microorganism results in slow rate of ethanol production and also difficulties such as complicated fermentation control because of the necessity of aeration, even though the fermentation is performed under anaerobic condition.

It is well known to use a strain belonging to Zymomonas as a fermentation microorganism (Japanese Patent Publication No. H7-59187).

It is recognized that a fermentation process by using Zymomonas leads to increased rate of ethanol production compare to that by using a yeast. Improvement of ethanol production efficiency by biotechnological modification of various microorganism species has been proposed (Japanese Patent Publication Nos. H5-502366, H6-504436, and H6-505875).

In the above technologies, 2 genes from *Zymomonas mobilis*, one encoding for PDC activity (which catalyses the conversion of pyruvic acid in the glycolytic pathway to acetoaldehyde) and another ADH activity (which catalyses the conversion of acetoaldehyde to ethanol) were inserted into host (enteric bacteria such as *Escherichia coli* or *Erwinia chrysanthe*) under a regulatory sequence allowing for their expression. Consequently, ethanol fermentation with high productivity was achieved by using such transformants.

According to the abovementioned technologies, improvement in ethanol productivity owes to the high growth and high cell density of the transformants in the fermentor. Such fermentation involving cell growth presents many inefficiencies including low conversion efficiency of sugar material to ethanol because the sugar material is used as an energy supply source for growth of said microorganism, low ethanol production rate during the period until the microorganism reaches stationary growth phase and complications in fermentor control due to the change of density of the microorganism accompanying the cell growth thereof.

Another technological problem is separation of toxic substances when *Escherichia coli* used as a host cell. *Escherichia coli* is succeptible to bacteriolysis leading to possible contamination of fermentation products with toxic intracellular protein.

From this point of view, improvement of host microorganism to be transformed is desirable.

Problem to be Solved by the Invention

The present invention provides a new process for producing ethanol by using biomass resources as raw material for sugars, wherein better excellent technology for efficiently producing ethanol at a high productivity has been accomplished and wherein various problems pointed out in the foregoing prior art have been solved.

Means to Solve the Problem

The present inventors have made extended studies to solve the problems mentioned above, and have found that efficient production of ethanol at a high productivity can be achieved by using a coryneform bacterium which has been transformed with a gene expressing PDC activity, and if desired, a gene expressing ADH activity under a regulatory sequence allowing for expression, and then, performing fermentation under ethanol production conditions wherein the transformed coryneform bacterium does not substantially proliferate, whereby the present invention has been accomplished.

One of the characteristics of the present invention is that a host bacterium to be transformed is a coryneform bacterium and that ethanol is prepared under conditions wherein the transformed coryneform bacterium does not substantially proliferate.

EMBODIMENT OF THE INVENTION

A gene expressing ADH activity and a gene expressing PDC activity from various microorganisms can be used in the present invention. Although each of the genes may be derived from different microorganisms, *Zymomonas mobilis* can be preferably used.

Specifically, the following gene, which have been already cloned and sequenced, can be used.

Genes Expressing ADH Activity
Origin *Zymomonas mobilis:*
　　ADHI gene (acc. NO. M32100) (J. Bacteriol. vol. 172, 2491-2492(1990))
　　ADHII gene (acc. NO. X17065, M15394) (J. Bacteriol. vol. 169,2591-2597(1987)).
Origin *Saccharomyces cerevisiae:*
　　ADH1 gene (J. Biol. Chem.vol.257,3018-3025(1982))
　　ADH2 gene (J. Biol. Chem.vol.258,2674-2682(1983))
　　ADH3 gene (Nature, vol.387,90-93(1997))
　　ADH4 gene (acc. NO. X05992) (Mol. Gen. Genet. vol. 209,374-381 (1987))
　　ADH5 gene (EMBO J. vol. 13,5795-5809(1994))
Origin *Sinorhizobium meliloti:*
　　ADH gene (Biochim. Biophys. Acta vol.1384,197-203 (1998))
Origin *Salmonella typhimurium:*
　　ADH gene (J. Bacteriol. vol.181(17),5317-5329(1999))

Origin *Mycobacterium tuberculosis*:
  ADH gene (Nature, vol. 393,537-544(1998))
Origin *Esherichia coli*:
  ADH gene (DNA Res. vol. 3,137-155(1996))

Genes Expressing PDC Activity
Origin *Zymomonas mobilis*:
  PDC gene (J. Bacteriol. vol. 170,3310-3313(1988))
Origin *Saccharomyces cerevisiae*:
  PDC1 (acc. NO. X77316) (Nucleic Acids Res.vol14, 893-63-8977(1986))
  PDC6 (acc. NO. X66843, X55905) (J. Bacteriol. vol. 173, 7963-7969 (1991))
  PDC5 (acc. NO. X15668)
  PDC2 (acc. No. X65608) (Mol. Gen. Genet. vol241,657-666(1993))
Origin *Bacillus subtilis*:
  pdhA gene/pdhB gene (acc. NO. AF012285) (J. Bacteriol. vol. 172, 5052-5063(1990))
Origin *Thiobacillus ferrooxidans*:
  pdhA gene/pdhB gene (acc. NO. U81808)(Microbiology, vol. 142, 2543-2548(1996)).

It is necessary for the two genes to be under a regulatory sequence in order to express their activity, although they are not necessarily required to be under a common regulatory sequence. They may be under separate regulatory sequences and in some cases on a different plasmids and at a different sites on a chromosome.

"Under a regulatory sequence" as used herein means that an intended gene can autonomously replicate by, for example, collaboratively acting with a promoter, inducer, operator, ribosome binding site and transcription terminator etc.

A host microorganism transformed according to the present invention is a coryneform bacterium. The coryneform bacterium is a Gram-positive bacterium and different from a Gram-negative bacterium such as *E. coli* which is used as a host bacterium in the aforementioned prior art. It is noteworthy that U.S. Pat. Nos. 5,482,846 and 5,916,787 disclosed a process for transforming a Gram-positive bacterium by a gene expressing ADH activity and PDC activity. However, the Gram-positive bacteria as used therein are Bacillus, Lactobacillus; Fibribacter, Ruminococcus, Pediococcus, Cytophaga, Cellulomonas, Bacteroides, Clostridium, *Bacillus subtilis*, and *Bacillus polymyxa,* but it is not taken into account that a coryneform bacterium can be used as the host cell to be transformed.

One of the major characteristics of the present invention is that a coryneform bacterium, which does not originally have a function of ethanol production from pyruvic acid, is selected as the host to be transformed. Use of coryneform bacterium transformed according to the present invention, enabled us to prepare ethanol under conditions in which no substantial cell growth was observed, in contrast to the usual process for producing ethanol by fermentation with yeast, Zymomonas or enteric bacteria such as *E. coli* transformed according to the aforementioned prior art.

Thus, by producing ethanol without cell growth, many technological problems resulting from cell growth as described above, are overcome. This has a significant value as a practical industrial production technology. The present inventors have discovered that such a technology can be achieved by using a coryneform bacterium.

Substantial suppression of growth of coryneform bacterium can be achieved by subjecting the aerobic bacterium to anaerobic conditions, or restricting the essential nutritional requirement, biotin (J. Industrial. Microbiol. vol.5,289-294. (1990)). In addition, biotechnological regulation of a function of a gene regulating growth would be an effective means.

Although ethanol fermentation under anaerobic condition has already been accomplished, the technology emphasizes or is accompanied by cell growth. On the contrary, the present invention is quite different to the extent that the present invention is intended to suppress the substantial growth of a coryneform bacterium in an ethanol reaction vessel.

The aforementioned prior art discloses that both anaerobic and aerobic conditions lead to an equivalent growth of a transformant and productivity of ethanol, which differs from the present invention in technological idea or content.

An essential element of the present invention is to introduce into a coryneform bacterium a DNA containing a gene expressing PDC activity and, if required, a gene expressing ADH activity under a regulatory sequence allowing for expression.

In this process, it is essential to introduce a gene expressing PDC activity, but not essential to introduce a gene expressing ADH activity. This is because usually a coryneform bacterium is deemed to have neither genes expressing the foregoing respective enzymes but it is uncertain regarding ADH. Thus, it cannot be denied that certain coryneform bacteria have the gene expressing ADH enzyme activity. In this case, it is basically enough to use only a gene expressing PDC enzyme activity as the gene to be introduced.

However, both genes are preferably introduced to effect higher transformation even if the coryneform bacterium used as a host originally has an ability to produce ADH.

There is no limitation as the type of aerobic coryneform bacteria transformed with the gene expressing PDC activity and, if desired, the gene expressing ADH activity, as long as it is a coryneform bacterium which is able to growth under usual aerobic conditions. Examples thereof are *Corynebacterium, Brevibacterium, Arthrobacter, Mycobacterium, and Micrococcus*. And more particularly, examples of *Corynebacterium* are *Corynebacterium glutamicum* ATCC13032, ATCC13058, ATCC13059, ATCC13060, ATCC13232, ATCC13286, ATCC13287, ATCC13655, ATCC13745, ATCC13746, ATCC13761, ATCC14020, and ATCC31831. Examples of *Brevibacterium* are *Brevibacterium lactofermentum* ATCC13869, *Brevibacterium flavum* MJ-233 (FERM BP-1497) and MJ-233AB-41 (FERM BP-1498), *Brevibacterium ammoniagenes* ATCC6872. Examples of *Arthrobacter* are. *Arthrobacter globiformis* ATCC8010, ATCC4336, ATCC21056, ATCC31250, ATCC31738 and ATCC35698.

As a transformation, there are processes for recombining a chromosome of a host bacterium with both genes, or a process to use a recombinant plasmid wherein both genes have been incorporated into a plasmid which can autonomously replicate in a host bacterium.

A plasmid vector used for such purposes may be one containing a gene with an autonomous replication function in a coryneform bacterium. As specific example, pAM330(Agric. Biol. Chem. vol. 48,2901-2903 (1984) and Nucleic Acids Symp Ser. Vol.16,265-267 (1985)) (from *Brevibacterium lactofermentum* 225), pHM1519(Agric. Biol. Chem. vol.48, 2901-2903(1984) (from *Corynebacterium glutamicum* ATCC13058), pCRY30(Appl. Environ. Microbiol. vol. 57, 759-764(1991)), pEKO, pEC5, pEKEx1 (Gene vol.102, 93-98 (1991)), and pCG4 (J. Bacteriol. Vol.159, 306-311 (1984))(from *Corynebacterium glutamicum* T250).

Construction of a plasmid used for transformation of coryneform bacteria in the present invention can be effected, for example, in the case of a gene from *Zymomonas mobilis* being used, by linking a regulatory sequence such as an appropriate promoter and terminator with DraI-DraI 1.4 kb gene fragment containing an intact ADH gene (J. Bacteriol. vol.169,2591-2597(1987)), and DraI-DraI 1.8 kb containing an intact PDC gene (J. Bacteriol. vol. 169,949-954(1987)) respectively, which is then inserted at an appropriate restriction site of any one of a plasmid vector as exemplified above.

An example of a promoter to express ADH gene and PDC gene in the aforementioned recombinant plasmid is, but not limited to, the one which is originally carried by a coryneform bacterium. It may be any base sequence which has a function to initiate the transcription of ADH gene and PDC gene. An example of a terminator which is put in the downstream of ADH gene and PDC gene under a regulatory sequence is, but not limited to, the one which is originally carried by a coryneform bacterium. It may be, for example, any base sequence having a function to terminate the transcription of ADH gene and PDC gene, such as the terminator for tryptophan operon from *E. coli*.

In the present invention, cultivation of the coryneform bacterium, which is performed prior to introduction of a plasmid vector containing such as the intended gene into the coryneform bacterium, can be performed under usual aerobic conditions. A medium used for cultivation of usual microorganism can be used as culture medium. For example, to a general medium containing natural nutrients such as meat extract, yeast extract, and peptone etc., solution of inorganic salt such as ammonium sulfate, potassium phosphate, and magnesium sulfate is added, if necessary.

A process for introducing a plasmid vector containing the intended gene after the foregoing cultivation includes, but is not limited to, electroporation and the $CaCl_2$ method as long as such process enables introduction of a gene into a coryneform bacterium. In an embodiment thereof, for example a known method can be used for an electrical pulsation (Agric. Biol. Chem. vol.54, 443-447 (1990), Res. Microbiol. vol. 144,181-185(1993)).

As for the introduction of the intended gene into a chromosome, a similar method is available, for example, technology such as that described in DNA sequence vol. 3,303-310 (1993) is available.

A method for selecting the transformed coryneform bacteria employs antibiotic resistance, whereby a gene encoding for the said resistance is introduced into a plasmid vector or a chromosome containing the intended gene, and then plating the transformed coryneform bacterium, onto a plate containing an appropriate concentration of the said antibiotic. As an embodiment thereof, for example a method as described in Agric. Biol. Chem. vol. 54,443-447 (1990), Res. Microbiol. vol. 144, 181-185 (1993) is available.

Basically, in order to use an aerobic coryneform bacterium for the process of preparing ethanol of the present invention, a large amount of transformed coryneform bacteria must be cultured under usual aerobic conditions first. The present cultivation can be performed in a similar manner as a cultivation of a coryneform bacterium prior to transformation.

Transformed coryneform bacteria of the present invention which were cultured under aerobic conditions are harvested by centrifugation, membrane filtration or chemically treated (for example, immobilization with carrageenan) in order to be used for a subsequent reaction to produce ethanol.

For the reaction to produce ethanol, an aqueous solution containing the appropriate inorganic salt or buffer is preferably used. To the aqueous solution, sugars, such as glucose which is material for ethanol production, are added.

The reaction to produce ethanol is performed under conditions wherein growth of the transformed aerobic coryneform bacterium is substantially suppressed. Various methods, as described above, can be employed to substantially suppress the growth, and it is adequate to put the transformed aerobic coryneform bacterium under anaerobic condition. A system for reaction to produce ethanol may be batchwise or continuous reaction, and preferably continuous in view of achieving high productivity. Use of continuous reaction system in the process of the present invention does not lead to substantial growth of the coryneform bacterium and therefore the operation control thereof is easier than that of a conventional method, which is accompanied by cell growth, Sugars used as raw material for ethanol production include, preferably, but are not limited to, glucose which leads to rapid ethanol production.

"Anaerobic conditions" as used herein means any conditions resulting in lowered concentration of dissolved oxygen in aqueous solution, provided that a trace amount of the dissolved oxygen should be allowed as long as growth of the transformed coryneform bacterium is substantially inhibited. This condition is achieved by, for example, carrying out the reaction without aeration in a sealed container, or performing the reaction while supplying an inert gas such as nitrogen. The temperature for ethanol production is usually 15° C.-45° C., and preferably 25° C.-37° C. pH during the reaction is adjusted to the range of 5-9, and preferably 7-8. The coryneform bacterium used for ethanol production in the present invention can be used at a very high concentration such as 1 g/l-1500 g/l because it is not substantially growing during the reaction.

In ethanol production of the present invention, the cells are not substantially growing during the reaction, and raw material sugars are not consumed as a source of nutrition for growth. In addition, no need for induction period such as the exponential growth phase for providing a high-density culture of bacteria means that ethanol production with high density (high concentration) of cells from the early stage of reaction is possible, thereby highly efficient ethanol production at a high productivity can be achieved.

Ethanol prepared according to the process as stated above is isolated from the reaction and purified, if necessary, and utilized as fuel ethanol or industrial raw chemical material.

The following examples illustrate the present invention in detail, but should not be deemed to limit the scope of the invention.

EXAMPLES

Example 1

Cloning of a DNA Containing ADH Gene-and PDC Gene Fragments from *Zymomonas mobilis* ATCC29191.

(A) Extraction of Total DNA from *Zymomonas mobilis* ATCC29191:

To 1L of a growth medium [Composition:20 g of Glucose, 5 g of Yeast Extract and 1000 ml of distilled water], a platinum loopful of *Zymomonas mobilis* was inoculated. It was then anaerobically cultured at 30° C. till at late exponential growth phase, and harvested.

Bacterial cell obtained were suspended at the concentration of 10 mg/ml to 15 ml of a solution containing 10 mg/ml lysozyme, 10 mM NaCl, 20 mM Tris buffer(pH 8.0) and 1 mM EDTA-2Na(the concentration of each components shows the final concentration). Then, protease K was added at the final concentration of 100 µg/ml, and heated at 37° C. for 1 hour. In addition, sodium dodecyl sulfate (SDS) was added to the final concentration of 0.5%, and kept warm to 50° C. for 6 hours to lead to bacteriolysis. To this bacteriolyzed solution, an equal amount of phenol/chloroform solution was added, gradually shaken at room temperature for 10 min, and then the total volume was centrifuged (5,000×g, 20 min,10-12° C.) to separate a fraction of supernatant. To this supernatant, sodium acetate was added to become at a concentration of 0.3 M, and then, double volume of ethanol was gradually added. DNA existing between a water layer and ethanol layer was taken up by glass rod, washed with 70% ethanol and then air-dried. To the DNA obtained, 5 ml of a solution of 10 mM Tris buffer (pH 7.5)-1 mM EDTA·2Na was added and allowed to stand over night at 4° C. followed by used for the subsequent experiments.

(B) Cloning of a DNA Fragment Containing ADH Gene and PDC Gene from *Zymomonas mobilis*:

PCR was conducted by using chromosomal DNA prepared in Example 1(A) as a template. In order to clone ADH gene and PDC gene In the PCR, the following each one pair of primers is synthesized by using "394 DNA/RNA synthesizer" (Applied Biosystems) and used.

ADH Gene-amplifying Primer (a-1) 5'—tct cga gct ctg tag ggt gag gtt ata gct—3' (SEQ ID NO: 1)

(b-1) 5'—ctc tgg tac ctc aag aca gga cgg aaa acc—3' (SEQ ID NO: 2)

Primer (a-1) contains SacI restriction site and primer b-1) contains KpnI restriction site.

PDC Gene-amplifying Primer (a-2) 5'—tct cga att ctt gaa tat atg gag taa gca—3'(SEQ ID NO: 3)

(b-2) 5'—tct cga gct caa act aga gga gct tgt taa—3'(SEQ ID NO: 4)

Primer (a-2) contains EcoRI restriction site and primer (b-2) contains SacI restriction site.

Actually, PCR was conducted under the following conditions by using "DNA thermal cycler" (Perkin Elmer Cetus Co., Ltd.) and Taq DNA Polymerase/TaKaRa Ex Taq (Takara Shuzo Co., Ltd.) as a reaction reagent.

| Reaction: | |
|---|---|
| (10×)PCR buffer | 10 μl |
| 1.25 mM dNTP mixture | 16 μl |
| Template DNA | 10 μl |
| (Content of DNA: less than 1 μM) | |
| Two primers as described above[*) ] | 1 μl |
| | (respectively) |
| (Final concentration: 0.25 μM) | |
| Recombinant Taq DNA Polymeraze | 0.5 μl |
| Sterilized water | 61.5 μl |

[*) ]When amplifying ADH gene, a combination of primers (a-1) and (b-1) was used, and when amplifying PDC gene a combination of primers (a-2) and (b-2) was used. The above components were mixed and 100 μl of the reaction was subjected to PCR.

| PCR Cycle: | | |
|---|---|---|
| Denaturation process: | 94° C. | 60 sec |
| Annealing process: | 52° C. | 60 sec |
| Extension process: | 72° C. | 120 sec |

One cycle consisting of the above processes was repeated thirty cycles.

Ten microliter of reaction prepared as stated above was subjected to an electrophoresis with 0.8% agalose gel, and about 1.2 kb of a DNA fragment was detected for ADH gene, and about 1.7 kb of a DNA fragment for PDC gene.

Example 2

Preparation of a Recombinant Coryneform bacterium by ADH Gene and PDC Gene from *Zymomonas mobilis*.

(A) Construction of Shuttle Vector:

Five microliter of about 3.0 kb HindIII-HpaI DNA fragment containing ORF1(rep)of plasmid pAM330 inherent to *Brevibacterium lactofermentum* ATCC13869 (Yamaguchi, R. et al., Agric. Biol. Chem. 50, 2771-2778 (1986), Japanese Patent Publication No. S58-67679) and 2 μl of plasmid pHSG398 (Takara Shuzo Co., Ltd.) which was cleaved with a restriction enzyme HindIII were mixed, to which each component of 1 μl of T4 DNA ligase 10× buffer, 1 unit of T4 DNA ligase was added, made 10 μl with sterilized distilled water, and reacted at 15° C. for 3 hours to combine.

By using plasmid mixture thus obtained and calcium chloride method [Journal of Molecular Biology, 53, 159(1970) ], *Escherichia coli* JM109(Takara Shuzo Co., Ltd.) was transformed, and was plated onto medium (10 g of tryptone, 5 g of yeast extract, 5 g of NaCl, and 16 g of agar were dissolved in 1 L of distilled water) containing 50 mg of chloramphenicol.

A strain grown on the medium was cultured in a liquid medium in a usual manner, plasmid DNA was extracted from the culture medium, and the plasmid was cleaved with a restriction enzyme to confirm the inserted fragment. As a result, in addition to 2.2 kb of DNA fragment of plasmid pHSG398 about 3.0 kb of the inserted DNA fragment was identified.

This *Escherichia coli*-coryneform bacterium shuttle vector is referred to as pKP1.

(B) Ligation of tac Promoter with ADH Gene and PDC Gene:

Five microliter of about 1.2 kb DNA fragment containing ADH gene from *Zymomonas mobilis* amplified in Example 1(B), and 2 μl of plasmid pTrc99A(Pharmacia) containing tac promoter were respectively cleaved with restriction enzymes SacI and KpnI, the restriction enzymes were inactivated by treating at 70° C. for 10 min, and then both are combined, to which each component consisting of 1 μl of T4 DNA ligase 10× buffer and 1 unit of T4 DNA ligase was added, made 10 μl with sterilized distilled water, and reacted at 15° C. for 3 hours to bind. This is used as ligation solution A.

Similarly, 5 μl of about 1.7 kb DNA fragment containing PDC gene from *Zymomonas mobilis* amplified in Example 1(B) and 2 μl of plasmid pTrc99A(Pharmacia) containing tac promoter were respectively cleaved with restriction enzymes EcoRI and SacI, and the restriction enzymes were inactivated by treating at 70° C. for 10 min and then both are combined, to which each component consisting of 1 μl of T4 DNA ligase 10× buffer and 1 unit of T4 DNA ligase was added, made 10 μl with sterilized distilled water, and reacted at 15° C. for 3 hours to ligate. This is used as ligation solution B.

By using each of two ligation solutions A and B, and calcium chloride method [Journal of Molecular Biology, 53, 159(1970)], *Escherichia coli* JM109 (Takara Shuzo Co., Ltd.) was respectively transformed and was spread on a medium (10 g of tryptone, 5 g of yeast extract, 5 g of NaCl and 16 g of agar were dissolved in 1 L of distilled water) containing 50 mg of ampicillin.

Each of strains grown on the media was cultured in a liquid medium, plasmid DNA was extracted from the culture medium, the plasmid was cleaved with restriction enzyme (SacI, KpnI) for ligation solution A, and with restriction enzyme (EcoRI, SacI) for ligation solution B respectively, and the inserted fragment was confirmed. As a result, in addition to about 4.2 kb of DNA fragment from plasmid pTrc99A, an inserted DNA fragment with 1.2 kb in length was identified for ADH gene (ligation solution A), and an inserted fragment with 1.7 kb in length for PDC gene (ligation solution B).

A plasmid containing ADH gene is referred to as pTrc99A-ADH, and a plasmid containing PDC gene is referred to as pTrc99A-PDC.

Then, in order to prepare a DNA fragment wherein ADH gene was linked to tac promoter and a DNA fragment wherein PDC gene was linked to tac promoter by using PCR method in which plasmid pTrc99A-ADH and plasmid pTrc99A-PDC were used as a template, the following each one pair of primers was synthesized by using "394 DNA/RNA synthesizer" (Applied Biosystems).

(a-3)5'—ctc tag atc tcc gac atc ata acg gtt ctg—3' (SEQ ID NO: 5)

(b-3)5'—ctt ctc tca tcc gcc aaa ca—3' (SEQ ID NO: 6)

In addition, primer (a-3) contains BglII restriction site.

Actually, PCR was conducted under the following conditions by using "DNA thermal cycler" (Perkin Elmer Cetus Co., Ltd.) and Taq DNA Polymerase/TaKaRa Ex Taq)(Takara Shuzo Co., Ltd.) as a reaction reagent.

| Reaction: | |
|---|---|
| (10×)PCR buffer | 10 µl |
| 1.25 mM dNTP mixture | 16 µl |
| Template DNA*) | 10 µl |
| (Content of DNA: less than 1 µM) | |
| Primers (a-3) and (b-3) as described above | 1 µl (respectively) |
| (Final concentration: 0.25 µM) | |
| Recombinant Taq DNA Polymerase | 0.5 µl |
| Sterilized water | 61.5 µl |

*)When amplifying a DNA fragment in which ADH gene is linked to tac promoter, plasmid pTrc99A-ADH was used as a template DNA, and when amplifying a DNA fragment in which PDC gene is linked to tac promoter, plasmid pTrc99A-PDC was used. The above components were mixed and 100 µl of the reaction was subjected to PCR.

| PCR Cycle: | | |
|---|---|---|
| Denaturation: | 94° C. | 60 sec |
| Annealing: | 52° C. | 60 sec |
| Extension: | 72° C. | 120 sec |

One cycle consisting of the above processes was repeated thirty cycles.

Ten microliter of reaction prepared as stated above was subjected to electrophoresis on 0.8% agalose gel, and about 1.4 kb of DNA fragment was detected for tac promoter-linked ADH gene, and about 1.9 kb of DNA fragment for tac promoter-linked PDC gene.

(C) Insertion of a DNA Fragment in which ADH Gene is Linked to tac Promoter, and a DNA Fragment in which PDC Gene is Linked to tac Promoter into a Shuttle Vector:

Five µl of reaction of about 1.9 kb of DNA fragment, wherein PDC gene was linked to tac promoter, of which amplified product was confirmed in the above Example 2(B) was completely cleaved with restriction enzymes BglII and BamHI, and 2 µl of plasmid pKP1 prepared in the above Example 2 (A) was completely cleaved with restriction enzyme BamHI respectively. After the restriction enzymes were inactivated by treating at 70° C. for 10 min, both are combined, to which each component consisting of 1 µl of T4 DNA ligase 10× buffer and 1 unit of T4 DNA ligase was added, made 10 µl with sterilized distilled water, and reacted at 15° C. for 3 hours to bind.

By using the obtained plasmid mixture and calcium chloride method [Journal of Molecular Biology, 53, 159(1970)], Escherichia coli JM109(Takara Shuzo Co., Ltd.) was transformed, and was spread on a medium (tryptone:10 g, yeast extract:5 g, NaCl:5 g and agar:16 g were dissolved in 1 L of distilled water) containing 50 mg of chloramphenicol.

A strain grown on this media was cultured in a liquid medium, plasmid DNA was extracted from the culture medium, the plasmid was cleaved with restriction enzyme, and the inserted fragment was confirmed. As a result, in addition to about 5.2 kb of DNA fragment from plasmid pKP1 prepared in the above Example 2(A), an inserted DNA fragment with about 1.9 kb in length was identified. This plasmid is referred to as pKP1-PDC. This plasmid has only one BamHI restriction site.

Five µl of reaction of about 1.4 kb of DNA fragment, wherein ADH gene was linked to tac promoter, of which amplified product was confirmed was completely cleaved with restriction enzymes BglII and BamHI, and 2 µl of the above plasmid pKP1-PDC was completely cleaved with restriction enzyme BamHI respectively. After the restriction enzymes were inactivated by treating at 70° C. for 10 min, both are combined, to which each component consisting of 1 µl of T4 DNA ligase 10× buffer and 1 unit of T4 DNA ligase was added, made 10 µl with sterilized distilled water, and reacted at 15° C. for 3 hours to bind.

By using the obtained plasmid mixture and calcium chloride method [Journal of Molecular Biology, 53, 159(1970)], Escherichia coli JM109(Takara Shuzo Co., Ltd.) was transformed and was spread on a medium (tryptone:10 g, yeast extract:5 g, NaCl:5 g and agar:16 g were dissolved in 1 L of distilled water) containing 50 mg of chloramphenicol.

A strain grown on this media was cultured in a liquid medium, plasmid DNA was extracted from the culture medium, the plasmid was cleaved with restriction enzyme, and then, the inserted fragment was confirmed. As a result, in addition to about 7.1 kb of DNA fragment from plasmid pKP1 prepared in the above Example 2(A), an inserted DNA fragment with about 1.4 kb in length was identified.

This plasmid was named pKP1-ADH (SEQ ID NO: 7).

(D) Transformation of Coryneform Bacterium:

The plasmid was introduced into Corynebacterium glutamicum ATCC13032 by using electrical pulse method (Y. Kurusu, et al., Agric. Biol. Chem. 54: 443-447. 1990 and A. A. Vertes, et al., Res. Microbiol. 144:181-185. 1993). A transformant thus obtained, Corynebacterium glutamicum pKP1-PDC-ADH/13032 was deposited with National Institute of Bioscience and Human Technology (1-3 Higashi 1-Chome, Tsukuba-shi, Ibaraki-ken, Japan) on Jun. 6, 2000 (accession No. FERM P-17887), and then transferred to the International Deposit under Budapest Treaty on May 31, 2001 (International Patent Organism Depositary, National Institute of Advanced Industrial Science and Technology, AIST Tsukuba Central 6, 1-1, Higashi 1-Chome, Tsukuba-shi, Ibaraki-ken, 305-8566, Japan, accession No. FERM BP-7621).

Example 3

Ethanol Production by *Corynebacterium glutamicum* ATCC13032 Transformant (*Corynebacterium glutamicum* pKP1-PDC-ADH/13032)

A medium consisting of urea:40 g, $(NH_4)_2SO_4$:140 g, $KH_2PO_4$:5.0 g, $K_2HPO_4$:5.0 g, $MgSO_4.7H_2O$:5.0 g, $FeSO_4.7H_2O$:200 mg, $MnSO_4.nH_2O$:200 mg, D-biotin:2000 μg, thiamine hydrochloride: 1000 μg, yeast extract: 10 g, casamino acids:10 g and distilled water:10 l(pH 6.6) was poured in 500 ml portion into 2 l Erlenmeyer flask, sterilized at 120° C. for 15 min, to which 40 ml of an sterilized aqueous solution of 50% glucose was added. To the medium, *Corynebacterium glutamicum* strain which was transformed by introducing the above pKP1-PDC-ADH plasmid(pKP1-PDC-ADH/13032)was inoculated and cultured at 33° C. for 24 hours with stirring (aerobic culture). After completion of culture, it was centrifuged (8000 g, 20 min) to herveste the bacterial cells. The total volume of the obtained bacterial cells were subjected to the following reactions.

Five hundred ml of reaction consisting of $(NH_4)_2SO_4$:23 g, $KH_2PO_4$:0.5 g, $K_2HPO_4$:0.5 g, $MgSO_4.7H_2O$:0.5 g,$FeSO_4.7H_2O$:20 mg, $MnSO_4.nH_2O$:20 mg, D-biotin:200 μg, thiamine hydrochloride:100 μg, sodium carbonate 20 g, distilled water:1000 ml was poured into 1 L jar fermentor and the above bacterial cells and 50% glucose solution 120 ml were added, which was reacted at 30° C. with slowly stirring (200 rpm) under sealed condition (anaerobic reaction). After 2 and 4 hours, the respective reactions were centrifuged (8000 rpm, 15 min, at 4° C.), and each of supernatants thus obtained was then subjected to gas chromatography to be revealed the ethanol production at the concentration of 3.79 and 6.96(g ethanol/l), respectively.

These results are shown in the following Table 1.

TABLE 1

| Reaction time (hr) | 2 | 4 |
|---|---|---|
| Concentration of produced ethanol (g ethanol/l) | 3.79 | 6.96 |
| Mean rate of ethanol production (g ethanol/l/hr) | 1.89 | 1.74 |

Example 4

Ethanol Production by using *Brevibacterium lactofermentum* ATCC13869 Transformant (pKP1-PDC-ADH/13869)

Plasmid pKP1-PDC-ADH prepared according to the method of Example 2 (C) was introduced into *Brevibacterium lactofermentum* ATCC13869 in a similar manner as the method of Example 2 (D). The obtained transformant, *Brevibacterium lactofermentum* pKP1-PDC-ADH/13869 was deposited with National Institute of Bioscience and Human Technology (1-3 Higashi 1-Chome, Tsukuba-shi, Ibaraki-ken, Japan) on Jun. 6, 2000 (accession No. FERM P-17888), and then transferred to the International Deposit under Budapest Treaty on May 31, 2001 (International Patent Organism Depositary, National Institute of Advanced Industrial Science and Technology, AIST Tsukuba Central 6, 1-1, Higashi 1-Chome, Tsukuba-shi, Ibaraki-ken, 305-8566, Japan, accession No. FERM BP-7622).

In a similar manner as the method of Example 3, the obtained coryneform bacterium transformant was aerobically cultured, and subjected to a reaction to anaerobically produce ethanol. After 4 hours, the concentration of ethanol in a reactor was 4.21(g ethanol/l). Thus, the mean rate of ethanol production is 1.05(g ethanol/l/hr).

Effect of the Invention

According to the present invention, reaction of an aerobic coryneform bacterium transformed with ADH gene and PDC gene under anaerobic condition allows efficiently producing ethanol at a high productivity.

Sequence Listing Free Text
SEQ ID NO: 1:
  A primer for amplifying ADH gene.
SEQ ID NO: 2:
  A primer for amplifying ADH gene.
SEQ ID NO: 3:
  A primer for amplifying PDC gene.
SEQ ID NO: 4:
  A primer for amplifying PDC gene.
SEQ ID NO: 5:
  A primer for amplifying ADH gene linking with tac promoter.
SEQ ID NO: 6:
  A primer for amplifying PDC gene linking with tac promoter.
SEQ ID NO: 7:
  *E. coli*/coryneform bacteria shuttle vector having PDC gene linking with tac promoter ADH gene linking with tac promoter.

The invention claimed is:

1. A process for producing ethanol in a coryneform bacterium selected from the group consisting of *Corynebacterium glutamicum* and *Brevibacterium lactofermentum* by using pyruvate produced from sugars via a metabolizing pathway in the coryneform bacterium, the process comprising:
   a) transforming the coryneform bacterium with a polynucleotide having the nucleic acid sequence of SEQ ID NO: 7, and
   b) culturing the transformed bacterium under anaerobic conditions in a medium containing 200 µg/l of biotin, wherein the transformed bacterium does not proliferate.

2. A process for producing ethanol in a coryneform bacterium comprising:
   a) transforming a coryneform bacterium selected from the group consisting of *Corynebacterium glutamicum* and *Brevibacterium lactofermentum* with a polynucleotide having the nucleic acid sequence of SEQ ID NO: 7,
   b) culturing the transformed coryneform bacterium under anaerobic conditions in a medium containing 200 µg/l of biotin, such that the transformed bacterium does not proliferate, and
   c) collecting the ethanol produced thereby.

* * * * *

SEQUENCE LISTING

```
<160> NUMBER OF SEQ ID NOS: 7

<210> SEQ ID NO 1
<211> LENGTH: 30
<212> TYPE: DNA
<213> ORGANISM: Artificial Sequence
<220> FEATURE:
<223> OTHER INFORMATION: A primer for amplifying ADH gene

<400> SEQUENCE: 1
tctcgagctc tgtagggtga ggttatagct                                          30
```

<210> SEQ ID NO 2
<211> LENGTH: 30
<212> TYPE: DNA
<213> ORGANISM: Artificial Sequence
<220> FEATURE:
<223> OTHER INFORMATION: A primer for amplifying ADH gene

<400> SEQUENCE: 2
ctctggtacc tcaagacagg acggaaaacc                                     30

<210> SEQ ID NO 3
<211> LENGTH: 30
<212> TYPE: DNA
<213> ORGANISM: Artificial Sequence
<220> FEATURE:
<223> OTHER INFORMATION: A primer for amplifying PDC gene

<400> SEQUENCE: 3
tctcgaattc ttgaatatat ggagtaagca                                     30

<210> SEQ ID NO 4
<211> LENGTH: 30
<212> TYPE: DNA
<213> ORGANISM: Artificial Sequence
<220> FEATURE:
<223> OTHER INFORMATION: A primer for amplifying PDC gene

<400> SEQUENCE: 4
tctcgagctc aaactagagg agcttgttaa                                     30

<210> SEQ ID NO 5
<211> LENGTH: 30
<212> TYPE: DNA
<213> ORGANISM: Artificial Sequence
<220> FEATURE:
<223> OTHER INFORMATION: A primer for amplifying ADH gene linking with
      tac promoter

<400> SEQUENCE: 5
ctctagatct ccgacatcat aacggttctg                                     30

<210> SEQ ID NO 6
<211> LENGTH: 20
<212> TYPE: DNA
<213> ORGANISM: Artificial Sequence
<220> FEATURE:
<223> OTHER INFORMATION: A primer for amplifying PDC gene linking with
      tac promoter

<400> SEQUENCE: 6
cttctctcat ccgccaaaca                                                20

<210> SEQ ID NO 7
<211> LENGTH: 8500
<212> TYPE: DNA
<213> ORGANISM: Artificial Sequence
<220> FEATURE:
<223> OTHER INFORMATION: E.coli/coryne-form bacteria shuttle vector
      having PDC gene linking with tac promoter ADH gene linking with
      tac promoter

<400> SEQUENCE: 7
aagcttactg gccgtcgttt tacaacgtcg tgactgggaa aaccctggcg ttacccaact     60
taatcgcctt gcagcacatc cccctttcgc cagctggcgt aatagcgaag aggcccgcac    120

-continued

```
cgatcgccct tcccaacagt tgcgcagcct gaatggcgaa tgagcttctt ccgcttcctc      180
gctcactgac tcgctgcgct cggtcgttcg gctgcggcga gcggtatcag ctcactcaaa      240
ggcggtaata cggttatcca cagaatcagg ggataacgca ggaaagaaca tgtgagcaaa      300
aggccagcaa aaggccagga accgtaaaaa ggccgcgttg ctggcgtttt tccataggct      360
ccgcccccct gacgagcatc acaaaaatcg acgctcaagt cagaggtggc gaaacccgac      420
aggactataa agataccagg cgtttccccc tggaagctcc ctcgtgcgct ctcctgttcc      480
gaccctgccg cttaccggat acctgtccgc ctttctccct tcgggaagcg tggcgctttc      540
tcaatgctca cgctgtaggt atctcagttc ggtgtaggtc gttcgctcca agctgggctg      600
tgtgcacgaa ccccccgttc agcccgaccg ctgcgcctta tccggtaact atcgtcttga      660
gtccaacccg gtaagacacg acttatcgcc actggcagca gccactggta acaggattag      720
cagagcgagg tatgtaggcg gtgctacaga gttcttgaag tggtggccta actacggcta      780
cactagaagg acagtatttg gtatctgcgc tctgctgaag ccagttacct tcggaaaaag      840
agttggtagc tcttgatccg gcaaacaaac caccgctggt agcggtggtt ttttttgtttg      900 caagcagcag attacgcgca gaaaaaaagg atcctttga tcttttctac      960 ggggtctgac gctcagtgga actccgtcga acggaagatc acttcgcaga taaataaat      1020 cctggtgtcc ctgttgatac cgggaagccc tgggccaact tttggcgaaa atgagacgtt      1080
gatcggcacg taagaggttc caactttcac cataatgaaa taagatcact accgggcgta      1140
ttttttgagt tatcgagatt ttcaggagct aaggaagcta aaatgagaa aaaaatcact      1200 ggatatacca ccgttgatat atcccaatgg catcgtaaag aacattttga ggcatttcag      1260
tcagttgctc aatgtaccta taaccagacc gttcagctgg atattacggc cttttaaag      1320 accgtaaaga aaaataagca caagttttat ccggccttta ttcacattct gcccgcctg      1380 atgaatgctc atccggaatt tcgtatggca atgaaagacg gtgagctggt gatatgggat      1440
agtgttcacc cttgttacac cgttttccat gagcaaactg aaacgttttc atcgctctgg      1500
agtgaatacc acgacgattt ccggcagttt ctacacatat attcgcaaga tgtggcgtgt      1560
tacggtgaaa acctggccta tttccctaaa gggtttattg agaatatgtt tttcgtctca      1620
gccaatccct gggtgagttt caccagtttt gatttaaacg tggccaatat ggacaacttc      1680 ttcgccccg ttttcaccat gggcaaatat tatacgcaag cgacaaggt gctgatgccg      1740 ctggcgattc aggttcatca tgccgtctgt gatggcttcc atgtcggcag aatgcttaat      1800
gaattacaac agtactgcga tgagtggcag ggcggggcgt aattttttta aggcagttat      1860
tggtgccctt aaacgcctgg tgctacgcct gaataagtga taataagcgg atgaatggca      1920
gaaattcagc ttggcccagt gccaagctcc aatacgcaaa ccgcctctcc ccgcgcgttg      1980
gccgattcat taatgcagct ggcacgacag gtttcccgac tggaaagcgg gcagtgagcg      2040
caacgcaatt aatgtgagtt agctcactca ttaggcaccc caggctttac actttatgct      2100
tccggctcgt atgttgtgtg gaattgtgag cggataacaa tttcacacag gaaacattg      2160 accatgatta cgccgaattc gagctcggta cctcgagatc tgcagcccgg gatctccgac      2220
atcataacgg ttctggcaaa tattctgaaa tgagctgttg acaattaatc atccggctcg      2280
tataatgtgt ggaattgtga gcggataaca atttcacaca ggaaacagac catgggaattc      2340 ttgaatatat ggagtaagca atgagttata ctgtcggtac ctatttagcg gagcggcttg      2400
tccagattgg tctcaagcat cacttcgcag tcgcgggcga ctacaacctc gtccttcttg      2460
acaacctgct tttgaacaaa acatggagc aggtttattg ctgtaacgaa ctgaactgcg      2520
```

-continued

```
gtttcagtgc agaaggttat gctcgtgcca aaggcgcagc agcagccgtc gttacctaca      2580
gcgttggtgc gcattccgca ttcgatgcta tcggtggcgc ctatgcagaa aaccttccgg      2640
ttatcctgat ctccggtgct ccgaacaaca acgaccacgc tgctggtcat gtgttgcatc      2700
atgctcttgg caaaaccgac tatcactatc agttggaaat ggccaagaac atcacggccg      2760
ccgctgaagc gatttacacc ccggaagaag ctccggctaa aatcgatcac gtgattaaaa      2820
ctgctctcgc gaagaagaag ccggtttatc tcgaaatcgc ttgcaacatt gcttccatgc      2880
cctgcgccgc tcctggaccg gcaagtgcat tgttcaatga cgaagccagc gacgaagcat      2940
ccttgaatgc agcggttgac gaaaccctga aattcatcgc caaccgcgac aaagttgccg      3000
tcctcgtcgg cagcaagctg cgcgctgctg gtgctgaaga agctgctgtt aaattcaccg      3060
acgctttggg cggtgcagtg gctactatgg ctgctgccaa gagcttcttc ccagaagaaa      3120
atccgcatta cattggtacc tcatggggcg aagtcagcta tccgggcgtt gaaaagacga      3180
tgaaagaagc cgatgcggtt atcgctctgg ctcctgtctt caacgactac tccaccactg      3240
gttggacgga tatccctgat cctaagaaac tggttctcgc tgaaccgcgt tctgtcgttg      3300
tcagacgcat tcgcttcccc agcgttcatc tgaaagacta tctgacccgt ttggctcaga      3360
aagtttccaa gaaaaccggt tctttggact tcttcaaatc cctcaatgca ggtgaactga      3420
agaaagccgc tccggctgat ccgagtgctc cgttggtcaa cgcagaaatc gcccgtcagg      3480
tcgaagctct tctgacccg aacacgacgg ttattgctga aaccggtgac tcttggttca      3540
atgctcagcg catgaagctc ccgaacgtg tcgcgttga atatgaaatg cagtggggtc      3600
acattggttg gtccgttcct gccgccttcg gttatgccgt cggtgctccg aacgtcgca      3660 acatcctcat ggttggtgat ggttccttcc agctgacggc tcaggaagtt gctcagatgg      3720
ttcgcctgaa actgccggtt atcatcttct tgatcaataa ctatggttac accatcgaag      3780
ttatgatcca tgatggtccg tacaacaaca tcaagaactg ggattatgcc ggtctgatgg      3840
aagtgttcaa cggtaacggt ggttatgaca gcggtgctgc taaaggcctg aaggctaaaa      3900
ccggtggcga actggcagaa gctatcaagg ttgctctggc aaaacaccgac ggcccaaccc      3960 tgatcgaatg cttcatcggt cgtgaagact gcactgaaga attggtcaaa tggggtaagc      4020
gcgttgctgc cgccaacagc cgtaagcctg ttaacaagct cctctagttt gagctcggta      4080
cccggggatc tccgacatca taacggttct ggcaaatatt ctgaaatgag ctgttgacaa      4140
ttaatcatcc ggctcgtata atgtgtggaa ttgtgagcgg ataacaattt cacacaggaa      4200
acagaccatg gaattcgagc tctgtagggt gaggttatag ctatggcttc ttcaactttt      4260
tatattcctt tcgtcaacga aatgggcgaa ggttcgcttg aaaaagcaat caaggatctt      4320
aacggcagcg gcttaaaaa tgcgctgatc gtttctgatg ctttcatgaa caaatccggt      4380
gttgtgaagc aggttgctga cctgttgaaa gcacagggta ttaattctgc tgtttatgat      4440
ggcgttatgc cgaacccgac tgttaccgca gttctggaag gccttaagat cctgaaggat      4500
aacaattcag acttcgtcat ctccctcggt ggtggttctc cccatgactg cgccaaagcc      4560
atcgctctgg tcgcaaccaa tggtggtgaa gtcaaagact acgaaggtat cgacaaatct      4620
aagaaacctg ccctgccttt gatgtcaatc aacacgacgg ctggtacggc ttctgaaatg      4680
acgcgtttct gcatcatcac tgatgaagtc cgtcacgtta agatggccat tgttgaccgt      4740
cacgttaccc cgatggttc cgtcaacgat cctctgttga tggttggtat gccaaaaggc      4800
ctgaccgccg ccaccggtat ggatgctctg acccacgcat ttgaagctta ttcttcaacg      4860
```

```
gcagctactc cgatcaccga tgcttgcgcc ttgaaggctg cgtccatgat cgctaagaat    4920
ctgaagaccg cttgcgacaa cggtaaggat atgccagctc gtgaagctat ggcttatgcc    4980
caattcctcg ctggtatggc cttcaacaac gcttcgcttg ttatgtcca tgctatggct    5040
caccagttgg gcggctacta caacctgccg catggtgtct gcaacgctgt tctgcttccg    5100
catgttctgg cttataacgc ctctgtcgtt gctggtcgtc tgaaagacgt tggtgttgct    5160
atgggtctcg atatcgccaa tctcggtgat aaagaaggcg cagaagccac cattcaggct    5220
gttcgcgatc tggctgcttc cattggtatt ccagcaaatc tgaccgagct gggtgctaag    5280
aaagaagatg tgccgcttct tgctgaccac gctctgaaag atgcttgtgc tctgaccaac    5340
ccgcgtcagg gtgatcagaa agaagttgaa gaactcttcc tgagcgcttt ctaatttcaa    5400
aacaggaaaa cggttttccg tcctgtcttg aggtacccgg ggatcctcta gagtcgacca    5460
acgtcaacaa ccaccccgc agcgttaagt tgccccgcca acagaaagga accaacacg    5520
aaacaacaac acaaaaggt ttcacagaaa aagcgtatg cgctaacgta tgccccgcag    5580
cacggcaaaa gcgcgttaag ccctagccca gccgcgcgta ggtattactc atgcccacta    5640
tggtgtgcac actgcccact acggtgtgca atctattcac gatgccaccc ccagatacag    5700
tgaagccccg ccaatccgaa ctagatcaga tcaacggggc aacccattgt ccccagcttt    5760
gattaggagc caggcacata acagcatgac agttccattc ctgatgaaat cagccattgt    5820
caacaacaag acccatcata gtttgccccc gcgacattga ccataaattc atcgcacaaa    5880
atatcgaacg gggtttatgc cgcttttagt gggtgcgaag aatagtctgc tcattacccg    5940
cgaacaccgc cgcattcaga tcacgcttag tagcgtcccc atgagtaggc agaaccgcgt    6000
ccaagtccac atcatccata acgatcatgc acggggtgga atccacaccc agacttgcca    6060
gcacctcatt agcgacacgt tgcgcagcgg ccacgtcctt agccttatcc acgcaatcta    6120
gaacgtactg cctaaccgcg aaatcagact gaatcagttt ccaatcatcg ggcttcacca    6180
aagcaacagc aacgcgggtt gattcgaccc gttccggtgc ttccagaccg gcgagcttgt    6240
acagttcttc ttccatttca cgacgtacat cagcgtctat gtaatcaatg cccaaagcac    6300
gcttagcccc acgtgaccag gacgaacgca ggttttaga accaacctca tactcacgcc    6360
accgagccac caaaacagcg tccatatcct cgccggcgtc gctttgatcg gccaacatat    6420
ccaacatctg aaacggcgtg tacgacccct tagacgcggt tttagtagcg gagccagtca    6480
gttcctgaga catgccctta gcgaggtagg ttgccatttt cgcagcgtct ccaccccagg    6540
tagacacctg atcaagtttg accccgtgct cacgcagtgg cgcgtccata ccggccttaa    6600
ccacaccagc agaccagcgg gaaaacatgg aatcctcaaa cgccttgagt tcatcgtcag    6660
acagtggacg atccaagaac aacagcatgt gcggtgcaag tgccaaccgt tcgcccaaga    6720
gtctgtgacc tcatagtcac tataggtgtg ctccaccccg taccgtgcac gttctttctt    6780
ccactgagat gttttcacca tcgaagagta cgcagtctta atacccagct ctcaacctgc    6840
gcaaatgact gtgagcggtt gtgtcgaaca gtgcccacaa acatcatgag cgcgccaccc    6900
gccgccaagt gattcttagt agcaatagcc agctcaatgc ggcgttcgcc catgacttcc    6960
aattcagcca gaggtgaccc ccagcgagag tgagagtttt gcagaccctc aaactgcgaa    7020
cgaccgttag acgaccagga caccgcaaca gcttcgtccc tgcgccacct atggcacccc    7080
gccagagcct tactattggt gatcttgtac atgacgtttt gcctacgcca cgccctagcg    7140
cgagtgacct tagaaccctc attgacctgc ggttccttag aggtgttcac ttctatttca    7200
gtgttaccta gacccgatgt tgtgcggggt tgcgcagtgc gagtttgtgc gggtgttgtg    7260
```

```
cccgttgtct tagctagtgc tatggttgtc aattgaaacc ccttcgggtt atgtggcccc    7320
cgtgcatatg agttggtagc tcgcacgggg gtttgtcttg tctagggaac tattaatttt    7380
tagtggtgtt tggtggccgc ctagcttggc tatgcgtgcc agcttacccg tactcaatgt    7440
taaagatttg catcgacatg ggagggttac gtgtccgata cctagggggg gtatccgcga    7500
ctaggtgccc cggtgctcac tgtctgtacc gcgcaagccc cacacccgc atggaccagg     7560 tcgtccgccc cctgcacccc cagcaatctg catgtacatg ttttacacat tagcacgaca    7620
tgactgcatg tgcatgcact gcatgcagac taggtaaata tgagtatgta cgactagtaa    7680
caggagcact gcacataatg aatgagttgc aggacaatgt ttgctacgca tgcgcatgac    7740
atatcgcagg aaagctacta gagtcttaaa gcatggcaac caaggcacag ctagaacagc    7800
aactacaaga agctcaacag gcactacagg cgcagcaagc gcaggcacaa gccaccatcg    7860
aagcactaga agcgcaggca aaggctaagc ccgtcgtggt caccgcacgc gttcctttgg    7920
cactacgtga ggacatgaag cgcgcaggca tgcagaacgg tgaaaacctc caagagttca    7980
tgatcgccgc gtttaccgag cggctagaaa agctcaccac caccgacaac gaggaaaaca    8040
atgtctaacc cactagttct ctttgcccac cgtgacccgg taaatgacgt gacgttcgag    8100
tgcattgagc acgccaccta cgacacactt tcacacgcta aagaccagat caccgcccaa    8160
atgcaagccc tagacgaaga agccgcccta ctgccctaat gggtgtttca tgggtgtttc    8220
cctagtgttt catggtgttt tcacctaagc tagggaattg cgcgagaagt cctccgaaca    8280
aaatcagcaa cccccggaac cacacagttc acggggttc ttctatgcca gaaatcagaa     8340
aggggaacca gtgaacgacc ccgaatattg gatcacagcg cagcaggtcg ccgcccgcgt    8400
agctctcacc ccggccacca ttaaaaagtg ggcaaacgag ggaaaaatca ccgcatacaa    8460
gatcggcaag tccgtccgat tcaaagcatc agacgtagac                          8500
```